(12) United States Patent
Edelman et al.

(10) Patent No.: US 6,312,690 B1
(45) Date of Patent: Nov. 6, 2001

(54) MONOCLONAL RECOMBINANT ANTI-RHESUS D (D7C2) ANTIBODY

(75) Inventors: Léna Edelman, Boulogne; Christel Margaritte, Saint Orens; Michel Kaczorek, Montferrier; Hassan Chaabihi, Boisset et Gaujac, all of (FR)

(73) Assignees: Institut Pasteur, Paris; Proteine Performance, Saint Christol les ales, both of (FR)

( * ) Notice: Subject to any disclaimer, the term of this patent is extended or adjusted under 35 U.S.C. 154(b) by 0 days.

(21) Appl. No.: 08/793,450

(22) PCT Filed: Sep. 1, 1995

(86) PCT No.: PCT/FR95/01143

§ 371 Date: Jul. 1, 1997

§ 102(e) Date: Jul. 1, 1997

(87) PCT Pub. No.: WO96/07740

PCT Pub. Date: Mar. 14, 1996

(30) Foreign Application Priority Data

Sep. 2, 1994 (FR) .................................... 94 10566

(51) Int. Cl.⁷ ........................ A61K 39/395; C07K 16/28; C07H 21/04; C12N 5/10
(52) U.S. Cl. .................................... 424/142.1; 424/133.1; 424/135.1; 424/152.1; 424/143.1; 424/800; 424/801; 435/320.1; 435/326; 435/328; 435/334; 435/348; 530/387.1; 530/387.3; 530/388.22; 530/866; 530/867; 530/388.15

(58) Field of Search ............................... 424/133.1, 135.1, 424/152.1, 143.1, 800, 801, 142.1; 435/69.6, 320.1, 326, 328, 334, 348; 530/387.1, 387.3, 388.22, 866, 867, 388.15; 536/23.53; 935/4, 15, 22, 66

(56) References Cited

U.S. PATENT DOCUMENTS 5,516,657 * 5/1996 Murphy et al. ..................... 435/69.3
5,843,439 * 12/1998 Anderson et al. ................ 424/133.1

OTHER PUBLICATIONS

Harris et al., TIBTECH, 22:42–44, 1993.*
Waldmann, Science, 252:1657–1662, 1991.*
Putlitz et al., BIO/Technology 8:651–654, 1990.*
Hasemann et al., PNAS USA, 87:3942–46, 1990.*

* cited by examiner

Primary Examiner—Ronald B. Schwadron
(74) Attorney, Agent, or Firm—Oblon, Spivak, McClelland, Maier & Neustadt, P.C.

(57) ABSTRACT

Cloning of DNA fragments which code for the light chain or the heavy chain variable domain of the D7C2 monoclonal antibody within a baculovirus. The invention also concerns the expression of these DNA fragments in insect host cells, the anti-rhesus D recombinant monoclonal antibody so obtained and its use.

28 Claims, 2 Drawing Sheets

MONOCLONAL RECOMBINANT ANTI-RHESUS D (D7C2) ANTIBODY

The present invention relates to the production, in insect cells, of an anti-Rhesus D recombinant monoclonal antibody.

The subjects whose red blood cells are agglutinated by alloantibodies directed against the D antigen, (which is one of the antigens of the RH system) are commonly designated by the term "Rhesus positive", or "Rh-positive", and the subjects whose red blood cells are not agglutinated by these alloantibodies by the term "Rhesus negative", or "Rh-negative".

The haemolytic disease of newborn is due, in the majority of cases, to the presence, in an Rh-negative mother, of anti-Rhesus D alloantibodies (the alloimmunization against other antigens of the RH system is a lot more rare), which cause in a Rhesus positive foetus a haemolytic anaemia which will require either transfusions in utero, or an exchange transfusion at birth in severe cases.

Alloimmunization of the mother occurs generally during a previous childbirth; foetal red blood cells pass into the maternal blood stream and induce immunization if the child is Rh-positive.

The prevention of haemolytic disease of newborn consists in injecting anti-Rhesus D antibodies into Rhesus negative women immediately after childbirth or an abortion.

Currently, the anti-Rhesus antibodies used for this purpose are polyclonal immunoglobulins obtained from Rhesus negative volunteer donors immunized on several occasions against Rh-positive red blood cells.

This poses problems, on the one hand because of the need to have a sufficient number of volunteers to satisfy the needs, and on the other hand because of the risks of contamination by viruses or other pathogens which might be present in the immunoglobulin preparations obtained from the blood of volunteers.

However, this mode of production has at present no alternative. Indeed, although there are trials to culture lymphoblastoid lines, derived from B lymphocytes transformed by the Epstein-Barr virus and secreting monoclonal antibodies, no product obtained from this type of culture has received marketing authorization because of the risks involved in the use of the Epstein-Barr virus.

In order to obtain a source of anti-Rhesus D immunoglobulins not exhibiting the disadvantages of the immunoglobulins used up until now, the inventors had as objective the production of a recombinant anti-Rhesus human monoclonal antibody in insect cells, using an expression vector derived from a baculovirus.

With this aim in view, the inventors first selected a line producing an anti-Rhesus D monoclonal antibody called D7C2. This antibody belongs to the class of the IgM's, agglutinate the red blood cells with a common Rhesus phenotype, the weak Rhesus, and most of the partial Rhesus with the exception of $D^{VI}$; this antibody binds to a 30 to 32 kDa of the membrane of the red blood cells.

The inventors then cloned the sequences encoding the variable regions of the heavy (H) and light (L) chains of D7C2, and constructed expression cassettes allowing the expression of each of the said sequences under the control of a strong baculovirus promoter.

The subject of the present invention is a DNA fragment, characterized in that it is chosen from the group consisting of:

a DNA fragment which comprises a sequence which encodes the variable region of the light chain of the D7C2 monoclonal antibody;

a DNA fragment which comprises a sequence which encodes the variable region of the heavy chain of the D7C2 monoclonal antibody.

"Sequence which encodes the variable region of the light chain of the D7C2 monoclonal antibody" is understood to mean, in particular, the sequence identified in the sequence listing in the annex under the number SEQ ID NO: 1, which encodes the polypeptide SEQ ID NO: 2.

"Sequence which encodes the variable region of the heavy chain of the D7C2 monoclonal antibody" is understood to mean, in particular, the sequence SEQ ID NO: 3 which encodes the polypeptide SEQ ID NO: 4.

However, it will appear to persons skilled in the art that this definition also covers sequences which are functionally equivalent to the sequences SEQ ID NO: 1 and SEQ ID NO: 3, namely, in particular:

any sequence encoding the polypeptides SEQ ID NO: 2 and SEQ ID NO: 4, and also sequences encoding the polypeptides which may differ from the polypeptides SEQ ID NO: 2 and SEQ ID NO: 4 in a few amino acids, on the condition that this variation is not situated at the level of a peptide sequence involved in the recognition of the epitope.

This covers, for example, a sequence encoding a polypeptide whose sequence differs from that of the polypeptide SEQ ID NO: 4 in the replacement of the Thr residue at position 23, by a residue Ala, which results from the replacement of an A at position 67 in the sequence SEQ ID NO: 3, by a G.

Sequences which are functionally equivalent to the sequences SEQ ID NO: 1 and SEQ ID NO: 3, are also sequences resulting from a modification of the ends thereof for the purpose of creating restriction sites therein, or of modifying or suppressing those which are present therein. This covers, for example, a sequence encoding a polypeptide whose sequence differs from that of the polypeptide SEQ ID NO: 2 in the replacement of the first three residues, Asp-Ile-Glu, by the residues Gln-Ser-Val, which results from the replacement of an A at position 67 in the sequence SEQ ID NO: 3, by a G.

The subject of the present invention is also an expression cassette comprising a sequence encoding the variable region of the light chain of the D7C2 monoclonal antibody, or a sequence encoding the variable region of the heavy chain of the D7C2 monoclonal antibody, which sequence is placed under the transcriptional control of an appropriate promoter.

According to a preferred embodiment of the present invention, the said promoter is a baculovirus promoter.

By way of example of baculovirus promoters which can be used for carrying out the present invention, there may be mentioned the polyhedrin and P10 promoters of the baculoviruses AcMNPV or SlMNPV, or derivatives of baculovirus promoters, consisting of synthetic or recombinant promoters, obtained from a baculovirus promoter, and which are functional in insect cells, such as for example that described by WANG et al., [Gene, 100, 131–137, (1991)].

An expression cassette in accordance with this embodiment comprises, for example:

a baculovirus promoter as defined above;

a sequence encoding a secretory signal peptide;

a sequence encoding the variable domain of the light chain of the D7C2 monoclonal antibody and a sequence encoding the constant domain of the light chain of an immunoglobulin; or a sequence encoding the variable domain of the heavy chain of the D7C2 monoclonal antibody and a sequence encoding the constant domain of the heavy chain of an immunoglobulin.

A large number of sequences encoding signal peptides which are functional in insect cells can be used to carry out the present invention. By way of nonlimiting example, there may be mentioned the sequences encoding the signal peptides of Drosophila acetylcholinesterase, of ovine trophoblastin, as well as the sequences encoding the signal peptides of the H and L chains of murine or human immunoglobulins and the like.

Each of the cassettes in accordance with the invention allows the expression, either of the light chain, or of the heavy chain, of a recombinant antibody, called hereinafter r-D7C2, having the specificity of the D7C2 monoclonal antibody.

According to a preferred feature of this embodiment, the sequences encoding the constant domains of the light and heavy immunoglobulin chains are sequences of human origin.

The sequence encoding the constant domain of the light chain may be chosen from the sequences encoding the constant domains of the kappa (κ) and lambda (λ) light chains.

The sequence encoding the constant domain of the heavy chain may be chosen from the sequences encoding the constant domains of the heavy chains γ1, γ2, γ3, γ4, α, ε, and μ. There may thus be obtained a recombinant antibody belonging to the desired immunoglobulin class (IgG1, IgG2, IgG3, IgG4, IgA, IgE, IgM).

Most advantageously, a sequence encoding the constant domain Cγ of a γ heavy chain will be chosen. The recombinant antibody r-D7C2 thereby obtained belongs to class Ia IgG's, and will be called hereinafter r-IgG-D7C2.

The sequences encoding the light chain and the heavy chain of an antibody r-IgG-D7C2, of IgG1 isotype, are represented in the sequence listing in the annex under the numbers SEQ ID NO: 5 and SEQ ID NO: 7, respectively; the corresponding polypeptide sequences carry the respective identification numbers SEQ ID NO: 6 and SEQ ID NO: 8.

The subject of the present invention is also recombinant vectors carrying at least one expression cassette as defined above; in this context, the present invention includes in particular recombinant baculoviruses allowing the expression of the r-D7C2 antibody, as well as transfer plasmids allowing the construction of the said recombinant baculoviruses.

The transfer plasmids in accordance with the invention carry an insert comprising: an expression cassette as defined above, and on either side of this cassette, baculovirus sequences homologous to those of the regions flanking the viral genome portion for whose replacement it is desired to insert the said cassette.

According to a preferred embodiment of the transfer plasmids in accordance with the present invention, the said baculovirus sequences are homologous to those of the regions flanking the plo gene, or homologous to those of the regions flanking the polyhedrin gene.

According to a particularly advantageous feature of this embodiment, the expression cassette containing the gene encoding the light chain of the r-D7C2 antibody is flanked by the regions surrounding the polyhedrin gene in the wild-type baculovirus, and the expression cassette carrying the gene encoding the heavy chain of the r-D7C2 antibody is flanked by the regions surrounding the Plo gene in the wild-type baculovirus.

Briefly, the construction of the transfer plasmids in accordance with the invention is carried out by inserting into a plasmid capable of replicating in a bacterial host (in general E. coli), the region of the baculovirus gene (for example p10 or polyhedrin, or any other baculovirus locus) in whose place it is desired to insert the genes encoding the immunoglobulin H or L chains. In this region, the coding sequence of the baculovirus gene (and optionally the promoter sequence of the said gene) is replaced by the sequence encoding the immunoglobulin chain to be expressed (and optionally by the sequence of the promoter under whose control it is desired to express this immunoglobulin chain, if it is for example a "derived" promoter). The transfer plasmid thus obtained therefore contains an insert comprising a heterologous sequence (sequence of an r-D7C2 antibody chain) flanked by baculovirus sequences.

To allow the simultaneous expression of the heavy chain (H chain) and of the light chain (L chain) and their reassociation to form the recombinant antibody molecule, the inventors inserted both cassettes on the same expression vector. They thus obtained a double recombinant baculovirus in which the coding sequence of each of the H and L chains is under the control of a strong promoter.

A recombinant baculovirus in accordance with the invention, allowing the expression of the r-D7C2 antibody, may be constructed according to the following principle:

two transfer plasmids, as defined above, are prepared separately: one for the H chain, and one for the L chain.

Insect cells are then cotransfected with the DNA of the transfer vectors thus produced and the baculovirus DNA. This cotransfection is carried out in two stages:

The transfer plasmid containing the expression cassette for the light chain gene, flanked by regions surrounding the polyhedrin gene in the wild-type baculovirus, is used, with wild-type baculovirus AcMNPV DNA, to cotransfect insect cells in culture.

By homologous recombination between the viral DNA and the plasmid, the coding sequences of the recombinant immunoglobulin light chain are transferred into the viral genome.

After replication of the viral DNA in the transfected cells, the recombinant baculoviruses which have integrated the sequence of the recombinant immunoglobulin light chain are selected.

These recombinant baculoviruses are selected according to two criteria: their incapacity to produce polyhedra and their capacity to express the light chain.

In a second stage, the cells are cotransfected with the DNA of the recombinant baculovirus obtained at the end of the first stage, and with that of the transfer plasmid containing the expression cassette carrying the gene encoding the heavy chain of the r-D7C2 recombinant antibody flanked by the regions surrounding the baculovirus P10 gene. By homologous recombination, as above, the gene for the heavy chain is transferred into the viral DNA.

The double recombinant viruses which are capable of simultaneously producing an immunoglobulin heavy chain and light chain are then selected. The detection of the immunoglobulin heavy chain and light chain is carried out by ELISA.

Figure 2:
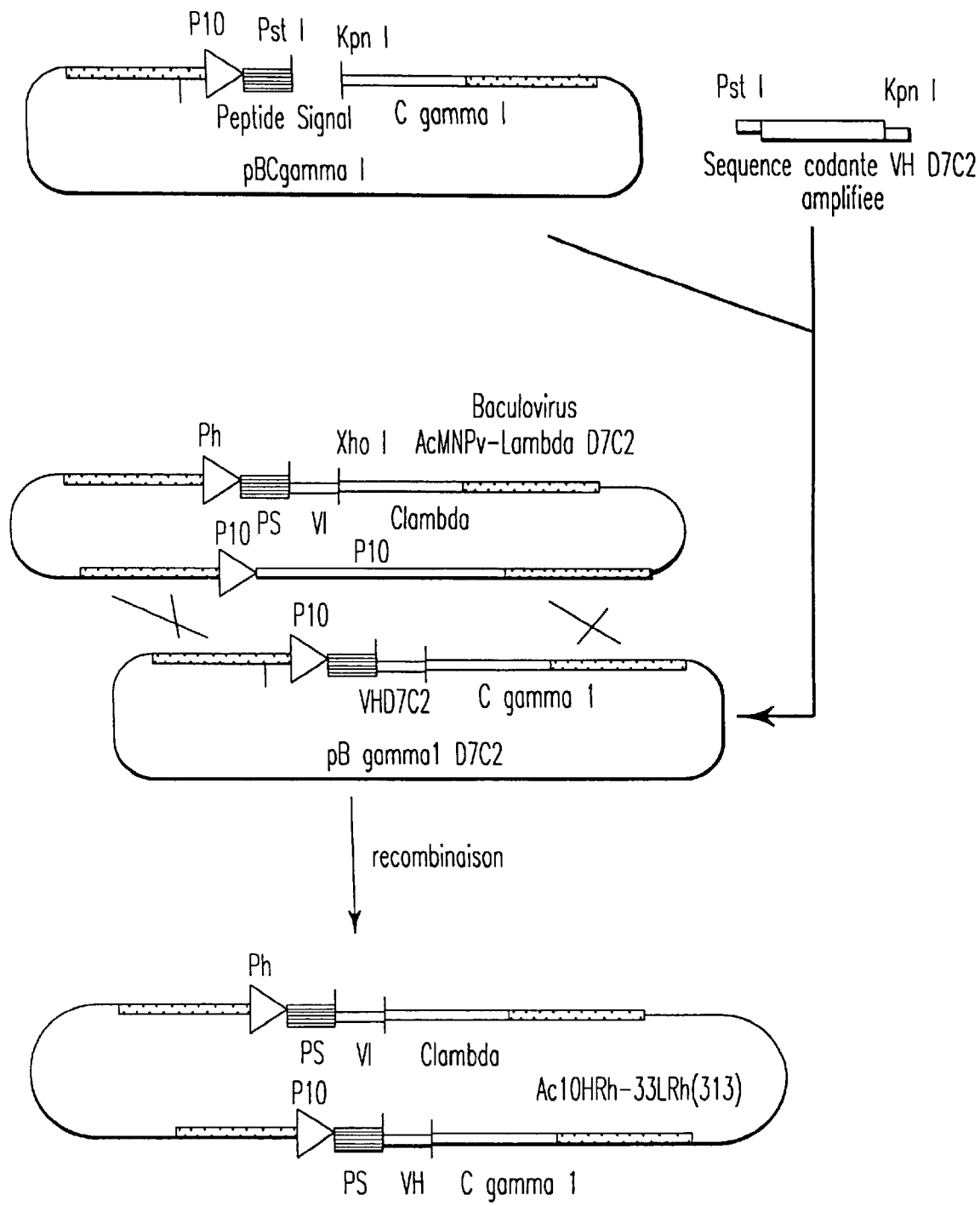

FIG. 2 illustrates this second stage which makes it possible to obtain a baculovirus expressing the lambda light chain and the gamma heavy chain of the r-IgG-D7C2 recombinant antibody.

The subject of the present invention is a recombinant baculovirus characterized in that it comprises at least one expression cassette, as defined above, comprising a sequence encoding all or part of the H chain or a sequence encoding all or part of the L chain of the r-D7C2 antibody, which sequence is placed under the transcriptional control of a strong baculovirus promoter.

According to one embodiment of a recombinant baculovirus in accordance with the invention, it comprises an expression cassette comprising the sequence encoding the H chain and an expression cassette comprising the sequence encoding the L chain, of the r-D7C2 monoclonal antibody.

According to a preferred feature of this embodiment, the promoter controlling the transcription of the sequence encoding the L chain of the r-D7C2 monoclonal antibody, and the promoter controlling the transcription of the sequence encoding the H chain of the r-D7C2 monoclonal antibody, are two different promoters.

According to an advantageous aspect of this feature, one of the said promoters is situated at the site occupied in the wild-type baculovirus by the polyhedrin promoter and the other is situated at the site occupied in the wild-type baculovirus by the P10 promoter.

According to yet another advantageous aspect of this feature, one of the promoters is the polyhedrin promoter or one of its derivatives, and the other is the p10 promoter or one of its derivatives.

Advantageously, the promoter controlling the transcription of the sequence encoding the light chain of the r-D7C2 antibody is the polyhedrin promoter or one of its derivatives, and the promoter controlling the transcription of the sequence encoding the heavy chain of the r-D7C2 antibody is the P10 promoter or one of its derivatives.

According to another feature of this embodiment, the sequence encoding the signal peptide associated with the L chain of the r-D7C2 monoclonal antibody, and the sequence encoding the signal peptide associated with the H chain or the r-D7C2 monoclonal antibody, are two different sequences.

A recombinant baculovirus in accordance with the invention, which comprises an expression cassette comprising the sequence encoding the $\lambda$ chain and an expression cassette comprising the sequence encoding the $\gamma 1$ chain of the r-IgG-D7C2 monoclonal antibody, was deposited on Aug. 19, 1994, at the C.N.C.M. (Collection Nationale de Cultures de Microorganismes, held by Institut Pasteur, 25 rue du Docteur ROUX, Paris), under the number I-1468.

The present invention also includes insect cells infected with a recombinant baculovirus in accordance with the invention.

The expression and production of the r-D7C2 recombinant monoclonal antibody is obtained in vitro in insect cells in accordance with the invention.

The infection of the cells by a double recombinant baculovirus in accordance with the invention results in the simultaneous production of the H and L chains. These chains assemble to reconstitute the r-D7C2 recombinant monoclonal antibody which is subsequently secreted into the culture medium.

The subject of the present invention is also a process for the preparation of a recombinant monoclonal antibody, characterized in that it comprises a stage during which insect cells infected with a recombinant baculovirus in accordance with the invention are cultured, and a stage during which the said antibody is obtained from the culture medium.

The subject of the present invention is also a recombinant monoclonal antibody, characterized in that its variable domains have the sequence of the variable domains of the D7C2 monoclonal antibody; this includes in particular the r-D7C2 recombinant monoclonal antibody preparations capable of being obtained by the process in accordance with the invention, which is defined above.

According to a preferred embodiment of the r-D7C2 recombinant monoclonal antibody, it belongs to the IgG class.

According to a preferred feature of this embodiment, the said r-D7C2 antibody is of the IgG1 isotype.

A recombinant antibody in accordance with the invention may be used for diagnosis or for therapy. A particularly advantageous use relates to the production of medicaments intended for the prevention of the haemolytic disease of newborn.

For this purpose, there will be used in particular a recombinant antibody r-IgG-D7C2, of the IgG class, which has an ADCC effector activity, which the parental antibody D7C2, which is an IgM, lacks.

The production of an anti-Rhesus D monoclonal antibody in insect cells makes it possible to avoid the risks and the problems linked to the immunization of Rh-D negative male volunteers by injection of Rh-D positive human red blood cells, and to reduce the risks of contamination by viruses or other pathogens which might be present in the immunoglobulin preparations extracted from the blood of the volunteers.

In addition, this mode of production has the following advantages:

pharmaceutical safety: the use of baculovirus and insect cell lines does not carry the risk of adventitious viruses or of oncogenes which occurs when human lines are used;

standardization of the production process and of the product derived therefrom;

a practically inexhaustible source of supply.

The present invention will be understood better with the aid of the following additional description which refers to examples of preparation of recombinant baculoviruses in accordance with the invention, and to their use for the production of a recombinant antibody of the IgGi isotype, called hereinafter r-IgG-D7C2, in insect cells.

It should be clearly understood, however, that these examples are given solely by way of illustration of the subject of the invention and do not in any manner constitute a limitation thereto.

EXAMPLE 1

Production of the D7C2 Antibody, and Cloning of the Heavy and Light Chains

A) Description of the D7C2 antibody:

The D7C2 human line was obtained after immortalization, by the Epstein-Barr virus, of peripheral blood lymphocytes obtained from a Rhesus negative donor (dce/dce) immunized on 5 occasions with Rhesus positive red blood cells (DCe/DCe).

The antibody secreted by this line is of the IgM isotype. This antibody, which will be called hereinafter IgM-D7C2, agglutinates the red blood cells of Rhesus positive phenotype DCcee; DCCee, DccEE, Dccee, and does not agglutinate the Rhesus negative red blood cells ddccee, ddccee, ddccEe. It agglutinates the weak Rhesus, and most of the partial Rhesus (agglutination of DIIIa, DIIIc, DIVa, DVa, DVc, DVII and Rh33), with the exception of the DVI's. It agglutinates the LW(a−b+) red blood cells, and does not agglutinate the $r^G$ and Rhmod red blood cells. The immunoprecipitation tests carried out on preparations of DCe/DCe Rhesus positive red blood cell membranes solubilized with TRITON X-100 showed a binding of the IgM-D7C2 antibody with a polypeptide of about 30 to 32 Kda.

B) Cloning and Sequencing of the Variable Parts of the Heavy Chain and of the Light Chain Total RNA is extracted from the cells of the D7C2 clone using guanidine thiocyanate, and then precipitated with isopropanol. After removal of the DNA by digestion with DNAse, the RNA is precipitated with NaCl (0.2M final concentration).

The cDNA is synthesized from 1 µg of RNA with reverse transcription, using an oligo-dT primer.

The variable parts of the heavy (VH) and light (VL) chains are amplified by PCR (polymerase chain reaction) from 1 µg of single-stranded cDNA, using Taq DNA polymerase.

The primers used are the following:

```
* For VH:
VH1 (SEQ ID NO: 9):
CCTCAGTGAAGGTCTCCTGCAAGG;

VH2 (SEQ ID NO: 10):
TCCTGCGCTGGTGAAAGCCACACA;

VH3 (SEQ ID NO: 11):
GGTCCCTGAGACTCTCCTGTGCA;

VH4a (SEQ ID NO: 12):
TCGGAGACCCTGTCCCTCACCTGCA;

VH4b (SEQ ID NO: 13):
CGCTGTCTCTGGTTACTCCATCAG;

VH5 (SEQ ID NO: 14):
GAAAAAGCCCGGGGAGTCTCTGAA;

VH6 (SEQ ID NO: 15):
CCTGTGCCATCTCCGGGGACAGTG;

* For VL:
VλFW1 (SEQ ID NO: 16):
CAGTCTGTGCTGACTCAG;

Cλ (SEQ ID NO: 17):
CACACYAGTGTRGCCTGGTT.
```

Thirty amplification cycles were thus carried out.

After phosphorylation, the amplified fragment is purified on an agarose gel, and then ligated into the plasmid PTZ18R. The plasmid obtained is used to transform *Escherichia coli* KL1 blue.

The selection of the transformed bacteria is made by a test of resistance to ampicillin.

The nucleotide sequence of the inserts of the plasmid vectors respectively called PTZ-$V_L$ D7C2 and PTZ-$V_H$D7C2 is determined with the aid of the PROMEGA sequencing kit.

The sequence encoding the variable region of the light chain of the IgM-D7C2 human monoclonal antibody is represented in the sequence listing in the annex under the number SEQ ID NO: 1; the corresponding polypeptide sequence is represented in the sequence listing in the annex under the number SEQ ID NO: 2.

The sequence encoding the variable region of the heavy chain of the IgM-D7C2 human monoclonal antibody is represented in the sequence listing in the annex under the number SEQ ID NO: 3; the corresponding polypeptide sequence is represented in the sequence listing in the annex under the number SEQ ID NO: 4.

The positions of the CDRs (complementarity determinant regions) are indicated in the sequence characteristics SEQ ID NO: 1 and SEQ ID NO: 3.

EXAMPLE 2

Construction of Transfer Plasmids Carrying the D7C2 Variable Sequences

A) TRANSFER PLASMID FOR THE LAMBDA LIGHT CHAIN:

1) Production of the plasmid pBCλ a—Plasmid pGmAc116T:

This vector is derived from the plasmid pGmAc115T [ROYER et al., J. Virol., 66, 3230–3235, (1992)], itself derived from the plasmid pAc1 [CHAABIHI et al., J. Virol., 67, 2664–2671 (1993)] containing the EcoRI-I fragment of the Autographa californica nuclear polyhedrosis baculovirus (AcMNPV), and therefore the polyhedrin gene, and the sequences flanking the said gene. To obtain pGmAc116T, the plasmid pGmAc115T was deleted of a 1900 bp fragment extending from an EcoRI site situated upstream of the polyhedrin gene to a XhoI site situated 1900 bp downstream of this EcoRI site. 5 µg of the plasmid pGmAc115T were digested for 2 hours at 37° C. with 15 units of XhoI enzyme (BOEHRINGER), in a reaction volume of 50 µl and under the conditions recommended by the supplier. After phenol/chloroform extraction, the plasmid DNA was precipitated with alcohol. This DNA was then partially cut with EcoRI (BOEHRINGER) in a reaction volume of 50 µl in the presence of 0.5 unit of enzyme. The incubation was carried out at 37° C. for 20 minutes. After another phenol/chloroform extraction, the ends generated by the XhoI and EcoRI cuts were made blunt by the Klenow enzyme (BIOLABS) in the presence of 4 dNTPs according to the procedure recommended by the supplier. The plasmid DNA was finally precipitated with alcohol and incubated with T4 phage ligase (BOEHRINGER) under the conditions recommended by the supplier.

Competent *E.coli* bacteria were transformed with part of the ligation mixture; the screening of the colonies derived from this transformation made it possible to select the plasmid pGmAc116T. This plasmid contains a BqlII site downstream of the polyhedrin promoter.

b—Signal peptide:

The coding sequence chosen for the signal peptide was chemically synthesized in the form of two complementary oligonucleotides having ends allowing the insertion of the duplex into a BglII site. For the pairing, 15 µg of each of the two oligonucleotides are incubated in 50 µl of buffer (1 mM Tris pH 7.5, 0.1 mM EDTA), for 5 minutes on a water bath at 70° C. The bath is then allowed to cool to room temperature (22 to 25° C.): the product of pairing is used directly in the ligation reactions with the plasmid pGmAc116T previously cut with BglII.

The ligation conditions are the following:

1 µg of the plasmid pGmAc116T cut with BglII; 1 µg of the double-stranded oligonucleotide carrying the sequence encoding the signal peptide; 2 µl of 10×ligase buffer (BOEHRINGER); distilled water qs 19 µl; 1 unit (1 µl) of ligase (BOEHRINGER). The incubation is carried out at 22° C. for 2 hours; the ligation product is used to transform competent *E. coli* bacteria.

c—Cλ constant region:

The coding sequence of the constant region of the human λ light chain was amplified by PCR using, as template, cDNA from human B lymphocytes. The human lymphocytes (about $5 \times 10^8$) were prepared from 200 ml of blood using HISTOPAQUE® (SIGMA). Total RNA was extracted from these lymphocytes using a PHARMACIA kit (RNA extraction kit). The first cDNA strand was prepared from the total RNA with the aid of the "First-Strand cDNA synthesis kit" from PHARMACIA.

The PCR amplification of the Cλ region was carried out in the presence of the primer OPP-HuCλ3' complementary to the 3' end of the Cλ regions and providing the BglII restriction site and of the primer OPP-HuCλ5' complementary to the 5' end of the Cλ regions and providing the XhoI restriction site.

The sequences of the two primers are the following:

OPP-HuCλ3' (SEQ ID NO: 18):
    5'-CCT GTC AGA TCT ATG AAC ATT CTG TAG GGG-3' (BglII site underlined)

OPP-HuCλ5' (SEQ ID NO: 19):
    5'-CCG CCC TCC CTC GAG CTT CAA-3' (XhoI site underlined)

The amplification product was digested with BglII and XhoI before being cloned into the XhoI-BglII sites of the plasmid pGmAc carrying the sequence encoding the signal peptide.

The composition of the ligation mixture is the following:

1 µg of the plasmid pGmAc cut with XhoI and BglII; 200 ng of the Cλ fragment amplified and digested with BglII and XhoI, 2 µl of 10×ligase buffer (BOEHRINGER), distilled water qs 19 µl, 1 unit (1 µl) of ligase (BOEHRINGER).

The incubation is carried out at 22° C. for 2 hours; the ligation product is used to transform competent E. coli bacteria.

The plasmid obtained is called pBCλ.

2) Cloning of the Variable Region of the λ Chain of D7C2

The cloning of the variable region of the λ light chain of the IgM-D7C2 human monoclonal antibody was carried out in the following manner:

The λ variable region of the IgM-D7C2 monoclonal antibody was amplified by PCR using:

as template, the DNA of the plasmid PTZ-$V_L$D7C2 described in Example 1 above, which carries the variable region of the light chain of the IgM-D7C2 monoclonal antibody;

a primer representing a consensus sequence at the 5' end of the human $V_L$ genes (OPP-HuVλ5'), and another primer complementary to the 5' region of the sequence encoding the lambda constant region (OPP-HuVλ3'), and which makes it possible to amplify any variable region of the λ chain).

These primers provide, in addition, the SacI and XhoI enzymatic restriction sites respectively.

The nucleotide sequences of these primers are the following:

OPP-HuVλ5' (SEQ ID NO: 20):
    5'-CA(GC)TCTGAGCTCAC(GT)CAG-3' (SacI site underlined)

The use of this primer causes the modification of the sequence Gln-Ser-Val of the first three amino acids of the structure 1 of the IgM-D7C2 parental antibody into Asp-Ile-Glu in the recombinant antibody.

OPP-HuVλ3' (SEQ ID NO: 21):
    5'-TTGAAGCTCGAGGGAGGGCGGGAA-3' (XhoI site underlined)

The composition of the amplification mixture is the following:

10 µl of 10×DNA polymerase buffer; 100 ng of plasmid PPTZ-$V_L$D7C2; 4 µl of the mixture of deoxynucleotides (mixture containing 5 mM DATP+5 mM dCTP+5 mM dGTP+5 mM dTTP, BOEHRINGER); 2 mM MgSO4; 1000 pmol of the primer OPP-HuVλ5' and 200 pmol of the primer OPP-HuVλ3'; 1 µl of thermostable DNA polymerase, and distilled water qs 100 µl.

The amplification was carried out over 30 successive cycles of incubation at 95° C. for 30 seconds, 40° C. for 30 seconds, and 72° C. for 30 seconds, and was then followed by an incubation at 72° C. for 10 minutes.

The amplification made it possible to obtain a fragment of about 360 bp containing the $V_L$ variable region of the D7C2 antibody as well as the sequence encoding the first 16 amino acids of the λ human constant region.

After amplification of the $V_L$ region, a digestion by the SacI and XhoI enzymes of the amplification product was carried out and the fragment obtained was inserted between the SacI and XhoI sites of the plasmid pBCλ to give the plasmid pBλD7C2. The composition of the ligation mixture is the following:

2 µl of 10×T4 DNA ligase buffer (BOEHRINGER); 100 ng of the $V_L$D7C2 fragment treated with the SacI and XhoI enzymes, 1 µl of the plasmid pBCλ cut with SacI and XhoI; 1 µl of ligase (1 unit), and distilled water qs 20 µl.

The incubation was carried out at 16° C. for 8 hours and then the ligation product was used to transform competent E. coli bacteria.

Figure 1:
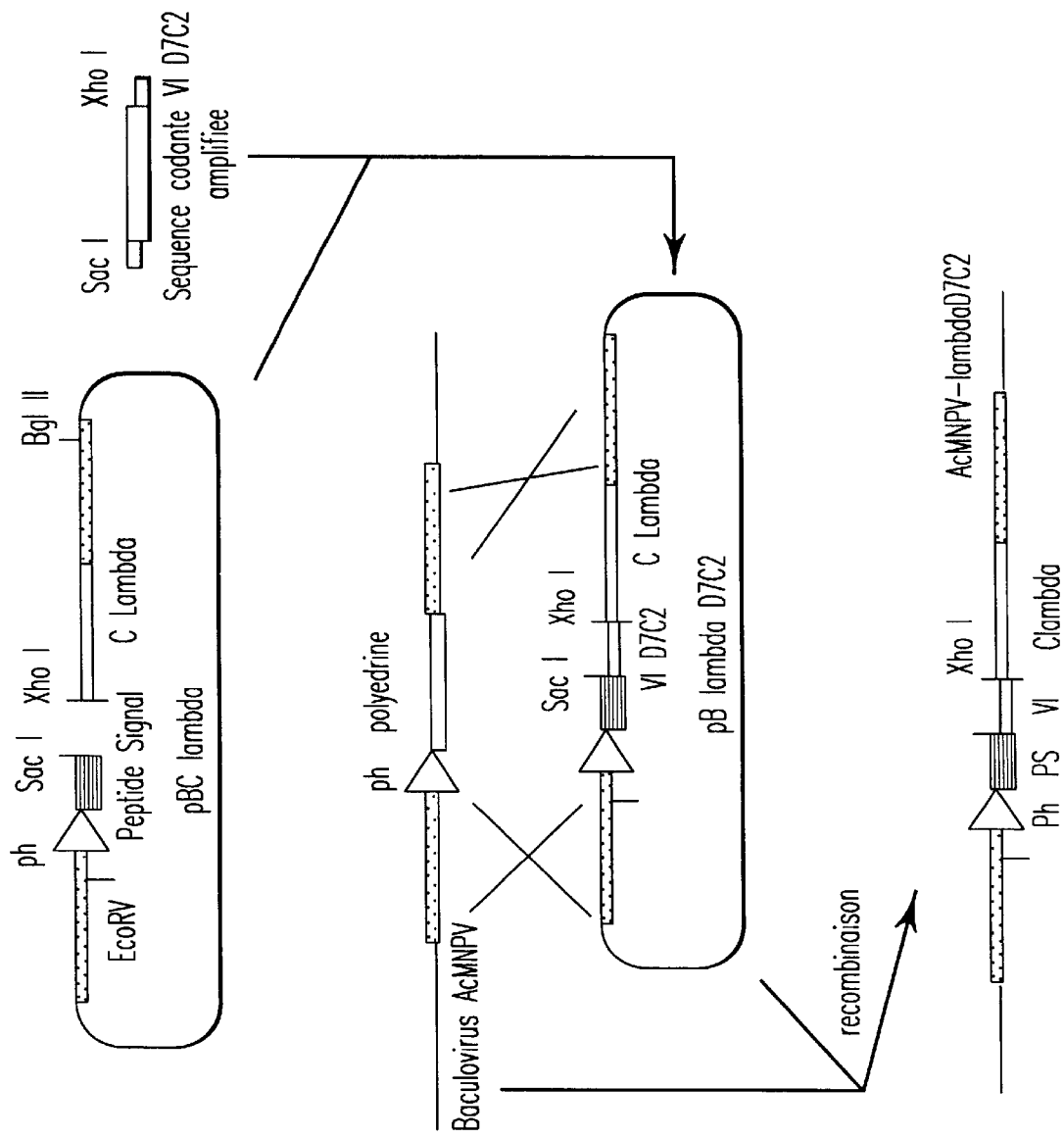
FIG. 1 illustrates the production of the baculovirus expressing the lambda light chain of the r-IgG-D7C2 recombinant antibody.

The stages of construction of the plasmid pBλD7C2 are represented in FIG. 1.

The sequence of the insert of the plasmid pBλD7C2 which encodes the lambda light chain of an r-D7C2 antibody, and which encodes the signal peptide, is represented in the sequence listing in the annex under the number SEQ ID NO: 5; the polypeptide sequence of the lambda light chain encoded by this insert is represented under the number SEQ ID NO: 6.

B) TRANSFER PLASMID FOR THE HEAVY CHAIN

1) Production of the plasmid pBCγ1 a—Transfer plasmid:

The plasmid pGm16 [BLANC et al., Virology, 192, 651–654, (1993)] is derived from a plasmid into which the EcoRI-P fragment of the AcMNPV baculovirus containing the p10 gene has been cloned. Practically the entire coding sequence was deleted and replaced by a BglII site allowing the insertion of sequences to be expressed under the control of the p10 promoter.

b—Signal peptide:

The coding sequence of this peptide is that of a mouse VH gene (NEUBERGER M. S., 1983. EMBO J., 2, 1373–1378).

It was chemically synthesized in the form of complementary strands, so that it can be inserted into a BglII site (FIG. 1). The pairing and ligation conditions are identical to those used for the light chain.

c—Human constant regions (Cγ1):

The cDNA of the coding sequence of the human Cγ1 region was amplified by PCR using the following primers:

HuCγ1BAC (SEQ ID NO: 22):
    5' GGT ACC ACG GTC ACC GTC TCC-3' (KpnI site underlined).

This primer corresponds to a consensus sequence of the murine JH regions (3' ends of the variable regions of the murine heavy chains), and comprises a KpnI site.

HuCγ1FOR (SEQ ID NO: 23):
  5'-GAAGATC TCA TTT ACC CGG AGA CAG GGA G-3' (BglII site underlined).

The sequence was determined from human Cγ1 sequences. The primer is complementary to the 3' end of the human Cγ1's, and makes it possible to reconstitute, after amplification, a BglII site downstream of the stop codon.

The template used to amplify the human Cγ1 region is the same cDNA mixture as that used for the amplification of the Cλ coding sequences.

The amplification product was sequenced and cloned into the transfer vector pGm16 carrying the sequence encoding the signal peptide. The construct obtained was called pBCγ1.

2) Cloning of the variable region of the heavy chain of the D7C2 antibody

The cloning of the VH variable region of the heavy chain of the D7C2 antibody was carried out in the following manner:

the $V_H$ variable region of the heavy chain of the IgM-D7C2 monoclonal antibody was amplified by PCR using:

as template the DNA of the plasmid PTZ-$V_H$D7C2 carrying the variable region of the heavy chain of the IgM-D7C2 monoclonal antibody, a primer reconstituting the 5' end of the variable regions of the VH4 family (OC15-HuVH4) and a second primer complementary to the 3' part of the human JH genes (OPP-HuJH). These primers provide the PstI and KpnI enzymatic restriction sites respectively.

The nucleotide sequences of these primers are the following:

OC15-HuVH4 (SEQ ID NO: 24):
  5'-GTC CAA CTG CAG CAG TGG GGC GCA GGA CTG TTG AAG CCT TCG GAG ACC CTG TCC CTC-3' (the PstI site is underlined)

This primer was determined in order to reconstitute the sequence encoding the first 14 amino acids of the structure 1 of the variable regions of the VH4 family of the human λ1 chains, which was missing from the plasmid PTZ-$V_H$D7C2.

OPP-HuJH (SEQ ID NO: 25):
  5'-TGA GGA GAC GGT GAC CGT GGT ACC TTG GC-3' (the KpnI site is underlined).

This primer is complementary to the consensus sequence at the 3' end of the human JH regions and comprises a KpnI site.

The composition of the amplification mixture is the following:

10 µl of 10×buffer for DNA polymerase, 100 ng of plasmid PTZ-$V_H$D7C2, 4 µl of the mixture of deoxynucleotides (mixture containing 5 mM DATP+5 mM dCTP+5 mM dGTP+5 mM dTTP, BOEHRINGER), 75 pmol of the primer OC15-HuVH4 and 100 pmol of the primer OPP-HuJH, 1 µl of thermostable DNA polymerase and distilled water qs 100 µl.

The amplification was carried out over 30 successive cycles of incubation at 95° C. for 30 seconds, 55° C. for 30 seconds and 72° C. for 30 seconds and was followed by an incubation at 72° C. for 10 minutes.

After amplification of the $V_H$D7C2 region, a PstI-KpnI digestion of the amplification fragment obtained (size about 360 bp) was carried out and the fragment obtained was inserted between the PstI and KpnI sites of the heavy chain cassette plasmid pBCγ1 to give the charged plasmid pBγ1D7C2.

The composition of the ligation mixture is the following:
  2 µl of 10×buffer for ligase (BOEHRINGER), 20 ng of the fragment V1D7C2 treated with the enzymes PstI and KpnI, 500 ng of the plasmid pBCλ1 cut with PstI and KpnI, 1 µl of ligase (BOEHRINGER) and distilled water qs 20 µl.

The ligation and the transformation of the competent E. coli bacteria are carried out as described above.

The stages of construction of the plasmid pBγ1D7C2 are represented in FIG. 2.

The sequence of the insert of the plasmid pBγ1D7C2 which encodes the gamma 1 heavy chain of an r-IgG-D7C2 antibody, and which encodes the signal peptide, is represented in the sequence listing in the annex under the number SEQ ID NO: 5; the polypeptide sequence of the gamma 1 heavy chain encoded by this insert is represented under the number SEQ ID NO: 6.

EXAMPLE 3

Construction of a Recombinant Baculovirus Producing the r-D7C2 Antibody a—Insertion of the Light Chain The charged plasmid pBλD7C2 was used to cotransfect insect cells with DNA of the wild-type baculovirus AcM-NPV.

The transfection conditions are the following: 500 ng of viral DNA and 4 µg of plasmid DNA in the presence of 40 µl of DOTAP (BOEHRINGER) in 3 ml of culture medium free of calf serum for insect cells. The cotransfection was carried out on 4×10⁶ Sf9 insect cells (ATCC35CRL 1711). After four hours of contact at 28° C., the cotransfection mixture is replaced by 4 ml of TGV5 medium (complete medium for insect cells with 5% calf serum). The culture is continued for 6 days at 28° C.

The virus producing the light chain of the r-IgG-D7C2 antibody under the control of the polyhedrin promoter was selected in a first instance based on its incapacity to produce polyhedra, and then on its capacity to express a light chain of about 25 kDa which is detectable by Western blotting with the aid of commercial anti-human λ chain antibodies (CALTAG, TEBU).

The DNA of the recombinant virus obtained (called AcMNPV-λD7C2) was prepared from infected cell supernatants.

b—Insertion of the Heavy Chain

The charged plasmid pBγ1D7C2 was used in cotransfection with the AcMNPV-λD7C2 modified baculovirus DNA. The cotransfection was performed with 500 ng of viral DNA and 5 µg of plasmid DNA, on Sf9 cells. The double recombinants were selected by the limiting dilution technique, combined with the ELISA technique.

After one week of culture, the cotransfection supernatant is diluted ($10^{-4}$ to $10^{-10}$), and then distributed into 96-well plates on Sf9 cells (100 µl of supernatant/well), after one hour of contact, 100 µl of medium are added to each well. The secretion of γ1 immunoglobulins is determined in the supernatant of each well by ELISA after one week of culture at 28° C.

The ELISA test is performed as indicated below:

50 µl of culture supernatant from each well are deposited on an ELISA plate (NUNC) coated with anti-total human IgG antibodies (CALTAG, TEBU). The adsorption of the anti-IgG antibodies (100 µl of a 1/2000 dilution per well) was performed in PBS buffer (137 mM NaCl; 2.7 mM KCl; 4.3 mM $Na_2HPO_4$; 1.4 mM $KH_2PO_4$) overnight at 4° C., after prior saturation for one hour at 37° C. with PBS supplemented with 5% calf serum. After the addition of the culture supernatants, 50 µl of PBS supplemented with 1% calf serum and 0.1% Tween 20 are added to each well. The whole is incubated at 37° C. and three washes with PBS supplemented with 1% Tween 20 are carried out. The plates are coated with anti-human IgG antibodies coupled to biotin (CALTAG), in an amount of 100 μl/well of a 1/10,000 dilution made in PBS supplemented with 1% calf serum and 0.1% Tween 20, for one hour at 37° C. After three new washes, the plates are incubated in the presence of streptavidin/alkaline phosphatase conjugate (1/10,000 dilution, CALTAG) and then revealed using the p-nitrophenyl phosphate substrate (1 mg/ml, SIGMA) diluted in alkaline buffer (9 volumes of 3M NaCl solution and 1 volume of 1M Tris-HCl buffer pH 9.6). The optical density is measured for each well by spectrophotometry at 405 nm. The supernatants of the wells which are positive at the highest viral dilutions are recovered and stored.

The isolation of a recombinant viral clone expressing the light chain and the heavy chain is performed by two other series of infections in 96-well plates and determination of the antibody by ELISA, followed by cloning by the lysis plaque technique. The virus selected was called Ac10HRh-33LRh (313).

EXAMPLE 4

Production and Purification of the r-IgG-D7C2 Recombinant Monoclonal Antibody a) Culture and Purification The virus selected Ac10HRh-33LRh (313) is multiplied on Sf9 insect cells in TGV2 medium (2% foetal calf serum). The concentration of antibody produced and secreted is evaluated by ELISA; it is about 3 mg/l.

A fraction of the viral supernatant obtained is concentrated 10 fold with the aid of CENTRIPREP 30 concentrators (AMICON), at a rotating speed of 1800 revolutions per minute. This concentrate is used directly for the tests of biological activity in vitro. The concentration of recombinant antibody is evaluated at 30 mg/l in the concentrate.

Moreover, a fraction (50 ml) of viral supernatant is deposited on a protein A chromatography column (SEPRACOR gel) previously equilibrated with PBS, in order to purify the recombinant IgG1. After two successive rinses of the column with PBS and a 0.1M citrate/citric acid solution pH5, the immunoglobulin is eluted with a 0.1M citrate/citric acid solution pH 3. The elution is monitored by measuring the OD at 280 nm. Finally, the fractions collected are neutralized to pH 7 with a Tris-HCl solution pH 8 and stored at 4° C. The solution of purified antibody is tested for the biological activity in parallel with the concentrated solution.

b) Control of the Assembly and of the Size of the Immunoglobulin Chains

The quality of the antibody produced by the recombinant virus Ac10HRh-33LRh (313) was controlled by electrophoretic migration in a 12.5% SDS-PAGE gel using, as control, a commercial monoclonal human IgGλ (SIGMA). This experiment showed that the nonreduced human antibody migrates to the same level as the control human antibody. After reduction with dithiotreitol (DTT), the appearance of two subunits corresponding to the heavy and light chains, and migrating to the same level as the control human antibody chains treated in the same manner, is observed.

To confirm these results, the proteins were transferred onto a nitrocellulose membrane, and the heavy and light chains were detected using specific anti-human IgG or anti-human λ antibodies.

EXAMPLE 5

Biological Activity of the r-IgG-D7C2 Recombinant Monoclonal Antibody

The biological activity of the recombinant antibody was measured using the culture supernatant of insect cells producing r-IgG-D7C2, concentrated 10 fold. The measurements were carried out in relation to the "irrelevant" recombinant antibody (IgG1, κ) directed against a protein other than the Rhesus antigen (negative control) and produced under the same conditions in insect cells, and in relation to the IgM-D7C2 human parental monoclonal antibody (IgM, λ).

The biological activity of the r-IgG-D7C2 recombinant antibody was evaluated:

1. By agglutination tests in tubes, with the insect cell culture supernatant concentrated 10 fold (30 μg/ml) and a panel of Rh-positive (R1/r, R1/R1, R2/R2, Ro/r) and Rh-negative (r/r) (G.N.R.G.S.) papain-treated human red blood cells.

50 μl of the concentrated culture supernatant, containing r-IgG-D7C2, and 50 μl of the suspension of 2% red blood cells were incubated for 45 minutes at 37° C.; the agglutinations were assessed as + to +++ according to the intensity of the reaction.

The results are presented in Table I below.

TABLE I

| PAPAIN-TREATED RED BLOOD CELLS | R1/r | R1/R1 | R2/R2 | Ro/r | r/r |
|---|---|---|---|---|---|
| INTENSITY | + | + | + + + | + + | − |

The r-IgG-D7C2 recombinant antibody titre, estimated by incubating the supernatant with a pool of red blood cells R1/r, treated with papain, for one hour at 37° C., is 1/512th.

2. By the ADCC test:

Effector cells (human lymphocytes):

The mononuclear layer is recovered from heparinized peripheral blood and separated on a Ficoll Hypaque gradient. The cells are incubated at 37° C., overnight, in a plastic cell culture dish (to suppress the monocytes) with 1% foetal calf serum; the nonadherent cells are then recovered and used for the cytotoxicity test in an amount of 8×10⁶ cells/ml.

Target cells (red blood cells)

The venous blood of normal donors, of the R1/R1 group (Rhesus positive) and of the r/r group (Rhesus negative), is collected over citrate, and then the red blood cells are suspended at 2% in NaCl and treated with papain.

Labelling with chromium $^{51}$Cr

20×10⁶ papain-treated red blood cells are incubated at 37° C. for one hour with 200 μCi of $^{51}$Cr, washed 4 times and resuspended in NaCl at 9 per thousand.

ADCC test

The experiments are carried out in triplicate, including the following combinations:

$^{51}$Cr-labelled red blood cells suspended in NaCl at 9 per thousand, in order to measure the spontaneous release of the chromium.

$^{15}$Cr-labelled red blood cells suspended in distilled water in order to measure the maximum release of chromium.

$^{51}$Cr-labelled red blood cells without antibody, in order to measure the possible cytotoxicity of the effector cells.

$^{51}$Cr-labelled red blood cells sensitized with:
  r-IgG-D7C2 recombinant anti-D;
  a specific polyclonal anti-D antibody (gammaglobulins, CNTS) as positive control;
  "irrelevant" recombinant antibody, as negative control.

The antibodies are used at two different concentrations (7.5 μg/ml, 3.5 μg/ml).

The prepared cells, effector cells and target cells are distributed in round-bottomed microplates in the following manner:

50 μl of lymphocytes (8×10⁶ cells/ml) and 50 μl of the suspension of $^{51}$Cr-labelled red blood cells (8×10⁵ cells/ml) are placed in each well with a ratio of 10/1; 50 μl of the different antibodies are then added for the comparative study.

The quantity of $^{51}$Cr released is measured for each suspension of red blood cells, and the % specific lysis is calculated according to the following formula:

$$\frac{(\% \text{ release for one test}) - (\% \text{ spontaneous release})}{(\% \text{ maximum release}) - (\% \text{ spontaneous release})} \times 100$$

The results are presented in Tables II (red blood cells R1/R1) and III (red blood cells r/r) below.

TABLE II

|  | Antibody concentration | % specific lysis |
| --- | --- | --- |
| Lymphocytes + red blood cells |  | 0.65% |
| Lymphocytes + red blood cells + recombinant control antibody (IgG1) | 3.5 μg/ml | 0% |
| Lymphocytes + red blood cells + r-IgG-D7C2 | 7.5 μg/ml | 76.6% |
|  | 3.5 μg/ml | 93.3% |
| Lymphocytes + red blood cells + polyclonal anti-D (γ-globulins) | 7.5 μg/ml | 66.9% |
|  | 3.5 μg/ml | 76.0% |

TABLE III

|  | Antibody concentration | % specific lysis |
| --- | --- | --- |
| Lymphocytes + red blood cells |  | 0.76% |
| Lymphocytes + red blood cells + recombinant control antibody (IgG1) | 3.5 μg/ml | 0% |
| Lymphocytes + red blood cells + r-IgG-D7C2 | 7.5 μg/ml | 1.3% |
|  | 3.5 μg/ml | 0% |
| Lymphocytes + red blood cells + polyclonal anti-D (γ-globulins) | 7.5 μg/ml | 0% |
|  | 3.5 μg/ml | 0.1% |

These results show that the r-IgG-d7C2 antibody induces a specific lysis of the Rh-positive red blood cells R1/R1.

What is claimed is:

1. A DNA fragment selected from the group consisting of:
   (a) a DNA fragment which encodes the variable domain of the light chain of the D7C2 monoclonal antibody, wherein the amino acid sequence of the variable domain is SEQ ID NO:2;
   (b) a DNA fragment which encodes the variable domain of the heavy chain of the D7C2 monoclonal antibody wherein the amino acid sequence of the variable domain is SEQ ID NO:4;
   (c) a DNA fragment which encodes the variable domain of the light chain of the D7C2 monoclonal antibody wherein the amino acid sequence of said variable domain is functionally equivalent to SEQ ID NO:2 and does not differ from SEQ ID NO:2 at a peptide sequence involved in the recognition of the epitope
   (d) DNA fragment which encodes the variable domain of the heavy chain of the D7C2 monoclonal antibody wherein the amino acid sequence of said variable domain is functionally equivalent to SEQ ID NO:2 and does not differ from SEQ ID NO:4 at a peptide sequence involved in the recognition of the epitope.

2. An expression cassette comprising at least one DNA fragment according to claim 1 and a DNA fragment encoding a constant domain of a light or heavy chain of an immunoglobulin, placed under the transcriptional control of a baculovirus promoter.

3. The expression cassette according to claim 2 comprising elements allowing the expression of the heavy chain or of the light chain of a recombinant monoclonal antibody called r-D7C2, said elements consisting of:
   (a) a baculovirus promoter, under whose transcriptional control are placed:
   (b) a sequence encoding a secretory signal peptide; and
   (c) a sequence encoding the variable domain of the light chain of the D7C2 monoclonal antibody and a sequence encoding the constant domain of the light chain of an immunoglobulin; or
   (d) a sequence encoding the variable domain of the heavy chain of the D7C2 monoclonal antibody and a sequence encoding the constant domain of the heavy chain of an immunoglobulin.

4. A recombinant vector comprising at least one DNA fragment according to claim 1.

5. A recombinant vector comprising at least one expression cassette according to claim 2.

6. A recombinant baculovirus comprising at least one expression cassette according to claim 2.

7. The recombinant baculovirus according to claim 6, comprising an expression cassette comprising the sequence encoding the H chain of the r-D7C2 antibody, and an expression cassette comprising the sequence encoding the L chain of the r-D7C2 antibody.

8. The recombinant baculovirus according to claim 7, wherein the promoter controlling the transcription of the sequence encoding the L chain of the r-D7C2 monoclonal antibody, and the promoter controlling the transcription of the sequence encoding the H chain of the r-D7C2 monoclonal antibody, are two different promoters.

9. The recombinant baculovirus according to claim 8, wherein one of said promoters is inserted at the site occupied in the wild-type baculovirus by the polyhedrin promoter and the other is inserted at the site occupied in the wild-type baculovirus by the p10 promoter.

10. The recombinant baculovirus according to claim 7, wherein the sequence encoding the signal peptide associated with the L chain of the r-D7C2 monoclonal antibody, and the sequence encoding the signal peptide associated with the H chain of the r-D7C2 monoclonal antibody, are two different sequences.

11. The recombinant baculovirus according to claim 10, deposited on Aug. 19, 1994, at the C.N.C.M, under the number I-1468.

12. Insect cells infected with a recombinant baculovirus according of claim 6.

13. A process for the preparation of a recombinant monoclonal antibody comprising:
   (a) culturing insect cells according to claim 12; and
   (b) obtaining said antibody from the culture medium.

14. A recombinant monoclonal antibody comprising variable domains having the sequence of the variable domains of the D7C2 monoclonal antibody wherein the sequences are encoded by the DNA of claim 1.

15. A recombinant monoclonal antibody, obtained by a process according to claim 13.

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 312 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(ix) FEATURE:
      (A) NAME/KEY: CDS
      (B) LOCATION: 1..312
      (D) OTHER INFORMATION: /product= "IMMUNOGLOBIN VARIABLE
          REGION"

(ix) FEATURE:
      (A) NAME/KEY: misc_feature
      (B) LOCATION: 67..99
      (D) OTHER INFORMATION: /label= CDR1

(ix) FEATURE:
      (A) NAME/KEY: misc_feature
      (B) LOCATION: 145..165
      (D) OTHER INFORMATION: /label= CDR2

(ix) FEATURE:
      (A) NAME/KEY: misc_feature
      (B) LOCATION: 262..279
      (D) OTHER INFORMATION: /label= CDR3

(xi) SEQUENCE DESCRIPTION: SEQ ID NO:1:

```
GAC ATC GAG CTC ACT CAG GAC CCT GCT GTG TCT GTG GCC TTG GGA CAG      48
Asp Ile Glu Leu Thr Gln Asp Pro Ala Val Ser Val Ala Leu Gly Gln
 1               5                  10                  15

ACA GTC AGG ATC ACA TGC CAA GGA GAC AGC CTC AGA ACC TAT TAT GCA      96
Thr Val Arg Ile Thr Cys Gln Gly Asp Ser Leu Arg Thr Tyr Tyr Ala
                20                  25                  30

AGC TGG TAC CAG CAG AAG CCA GGA CAG GCA CCT GTA CTT GTC ATC TAT     144
Ser Trp Tyr Gln Gln Lys Pro Gly Gln Ala Pro Val Leu Val Ile Tyr
         35                  40                  45

GGT AAA AAC AAC CGG CCC TCA GGG ATC CCA GAC CGA TTC TCT GGC TCC     192
Gly Lys Asn Asn Arg Pro Ser Gly Ile Pro Asp Arg Phe Ser Gly Ser
 50                  55                  60

AGC TCA GGA AAC ACA GCT TCC TTG ACC ATC ACT GGG GCT CAG GCG GAA     240
Ser Ser Gly Asn Thr Ala Ser Leu Thr Ile Thr Gly Ala Gln Ala Glu
 65                  70                  75                  80

GAT GAG GCT GAC TAT TTC TGT AAC AGC GGT GGG AAG GTG TTC GGC GGA     288
Asp Glu Ala Asp Tyr Phe Cys Asn Ser Gly Gly Lys Val Phe Gly Gly
                 85                  90                  95

GGG ACC AAG CTG ACC GTC CTA GGT                                     312
Gly Thr Lys Leu Thr Val Leu Gly
                100
```

(2) INFORMATION FOR SEQ ID NO:2:

(i) SEQUENCE CHARACTERISTICS:
      (A) LENGTH: 104 amino acids
      (B) TYPE: amino acid
      (D) TOPOLOGY: linear (ii) MOLECULE TYPE: protein (xi) SEQUENCE DESCRIPTION: SEQ ID NO:2:

Asp Ile Glu Leu Thr Gln Asp Pro Ala Val Ser Val Ala Leu Gly Gln
 1               5                  10                  15

Thr Val Arg Ile Thr Cys Gln Gly Asp Ser Leu Arg Thr Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
         50                  55                  60

Ser Ser Gly Asn Thr Ala Ser Leu Thr Ile Thr Gly Ala Gln Ala Glu
 65                  70                  75                  80

Asp Glu Ala Asp Tyr Phe Cys Asn Ser Gly Lys Val Phe Gly Gly
                 85                  90                  95

Gly Thr Lys Leu Thr Val Leu Gly
             100

(2) INFORMATION FOR SEQ ID NO:3:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..369
        (D) OTHER INFORMATION: /product= "IMMUNOGLOBIN VARIABLE
            REGION"

(ix) FEATURE:
        (A) NAME/KEY: misc_feature
        (B) LOCATION: 91..105
        (D) OTHER INFORMATION: /label= CDR1

(ix) FEATURE:
        (A) NAME/KEY: misc_feature
        (B) LOCATION: 148..195
        (D) OTHER INFORMATION: /label= CDR2

(ix) FEATURE:
        (A) NAME/KEY: misc_feature
        (B) LOCATION: 292..336
        (D) OTHER INFORMATION: /standard_name= "CDR3"

(xi) SEQUENCE DESCRIPTION: SEQ ID NO:3:

CAG GTC CAA CTG CAG CAG TGG GGC GCA GGA CTG TTG AAG CCT TCG GAG        48
Gln Val Gln Leu Gln Gln Trp Gly Ala Gly Leu Leu Lys Pro Ser Glu
 1               5                  10                  15

ACC CTG TCC CTC ACC TGC ACT GTC TAT GGT GGG TCC TTC AGT GGT TAC        96
Thr Leu Ser Leu Thr Cys Thr Val Tyr Gly Gly Ser Phe Ser Gly Tyr
                 20                  25                  30

TAC TGG AGC TGG ATC CGC CAG CCC CCA GGG AAG GGG CTG GAG TGG ATT       144
Tyr Trp Ser Trp Ile Arg Gln Pro Pro Gly Lys Gly Leu Glu Trp Ile
             35                  40                  45

GGG GAA ATC AAT CAT AGT GGA AGC ACC AAC TAC AAC CCG TCC CTC AAG       192
Gly Glu Ile Asn His Ser Gly Ser Thr Asn Tyr Asn Pro Ser Leu Lys
         50                  55                  60

AGT CGA GTC ACC ATA TCA GTA GAC ACG TCC AAG AAC CAG TTC TCC CTG       240
Ser Arg Val Thr Ile Ser Val Asp Thr Ser Lys Asn Gln Phe Ser Leu
 65                  70                  75                  80

AAA CTG AAC TCT GTG ACC GCC GCG GAC ACG GCT GTG TAT TAC TGT GCG       288

|     |     |     |     |     |     |     |     |     |     |     |     |     |
| --- | --- | --- | --- | --- | --- | --- | --- | --- | --- | --- | --- | --- |
| Lys | Leu | Asn | Ser | Val | Thr | Ala | Ala | Asp | Thr | Ala | Val | Tyr | Tyr | Cys | Ala |
|     |     |     |     | 85  |     |     |     | 90  |     |     |     | 95  |

```
AGG GCC CCA GAG TAT AAA TGG AAG TAT CAT GGG GAC TGG TTC GAC CCC      336
Arg Ala Pro Glu Tyr Lys Trp Lys Tyr His Gly Asp Trp Phe Asp Pro
            100                 105                 110

TGG GGC CAA GGT ACC ACT GTC ACC GTC TCC TCA                          369
Trp Gly Gln Gly Thr Thr Val Thr Val Ser Ser
        115                 120
```

(2) INFORMATION FOR SEQ ID NO:4:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:4:

```
Gln Val Gln Leu Gln Gln Trp Gly Ala Gly Leu Leu Lys Pro Ser Glu
 1               5                  10                  15

Thr Leu Ser Leu Thr Cys Thr Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Ala Pro Glu Tyr Lys Trp Lys Tyr His Gly Asp Trp Phe Asp Pro
            100                 105                 110

Trp Gly Gln Gly Thr Thr Val Thr Val Ser Ser
        115                 120
```

(2) INFORMATION FOR SEQ ID NO:5:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..716

(ix) FEATURE:
        (A) NAME/KEY: sig_peptide
        (B) LOCATION: 1..57

(ix) FEATURE:
        (A) NAME/KEY: mat_peptide
        (B) LOCATION: 58..716
        (D) OTHER INFORMATION: /product= "IMMUNOGLOBIN, LIGHT
            CHAIN"

(xi) SEQUENCE DESCRIPTION: SEQ ID NO:5:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
-19             -15                 -10                 -5

GTC CAC TCC GAC ATC GAG CTC ACT CAG GAC CCT GCT GTG TCT GTG GCC      96
```

```
Val His Ser Asp Ile Glu Leu Thr Gln Asp Pro Ala Val Ser Val Ala
         1               5                  10

TTG GGA CAG ACA GTC AGG ATC ACA TGC CAA GGA GAC AGC CTC AGA ACC    144
Leu Gly Gln Thr Val Arg Ile Thr Cys Gln Gly Asp Ser Leu Arg Thr
     15                  20                  25

TAT TAT GCA AGC TGG TAC CAG CAG AAG CCA GGA CAG GCA CCT GTA CTT    192
Tyr Tyr Ala Ser Trp Tyr Gln Gln Lys Pro Gly Gln Ala Pro Val Leu
 30                  35                  40                  45

GTC ATC TAT GGT AAA AAC AAC CGG CCC TCA GGG ATC CCA GAC CGA TTC    240
Val Ile Tyr Gly Lys Asn Asn Arg Pro Ser Gly Ile Pro Asp Arg Phe
                 50                  55                  60

TCT GGC TCC AGC TCA GGA AAC ACA GCT TCC TTG ACC ATC ACT GGG GCT    288
Ser Gly Ser Ser Ser Gly Asn Thr Ala Ser Leu Thr Ile Thr Gly Ala
             65                  70                  75

CAG GCG GAA GAT GAG GCT GAC TAT TTC TGT AAC AGC GGT GGG AAG GTG    336
Gln Ala Glu Asp Glu Ala Asp Tyr Phe Cys Asn Ser Gly Gly Lys Val
         80                  85                  90

TTC GGC GGA GGG ACC AAG CTG ACC GTC CTA GGT CAG CCC AAG GCT GCC    384
Phe Gly Gly Gly Thr Lys Leu Thr Val Leu Gly Gln Pro Lys Ala Ala
 95                 100                 105

CCC TCG GTC ACT CTG TTC CCG CCC TCC CTC GAG GAG CTT CAA GCC AAC    432
Pro Ser Val Thr Leu Phe Pro Pro Ser Leu Glu Glu Leu Gln Ala Asn
110                 115                 120                 125

AAG GCC ACA CTC GAG GAG CTT CAA GCC AAC AAG GCC ACA CTA GTG TGT    480
Lys Ala Thr Leu Glu Glu Leu Gln Ala Asn Lys Ala Thr Leu Val Cys
                130                 135                 140

CTG ATC AGT GAC TTC TAC CCG GGA GCT GTG ACA TTG GCT TGG AAG GCA    528
Leu Ile Ser Asp Phe Tyr Pro Gly Ala Val Thr Leu Ala Trp Lys Ala
            145                 150                 155

GAT GGC AGG CCC GTC AAG GCG GGA GTG GAG ACC AAC AAA CCC TCC AAA    576
Asp Gly Arg Pro Val Lys Ala Gly Val Glu Thr Asn Lys Pro Ser Lys
        160                 165                 170

CAG AGC AAC AAC AAG TAC GCG GCC AGC AGC TAC CTG AGC CTG ACG CCC    624
Gln Ser Asn Asn Lys Tyr Ala Ala Ser Ser Tyr Leu Ser Leu Thr Pro
    175                 180                 185

GAG CAG TGG AAG TCC CAC AGA AGC TAC AGC TGC CAG GTC ACG CAT GAA    672
Glu Gln Trp Lys Ser His Arg Ser Tyr Ser Cys Gln Val Thr His Glu
190                 195                 200                 205

GGG AGC ACT GCA GAG AAG ACG GTG GCC CCT GCA GAA TGT TCA TA         716
Gly Ser Thr Ala Glu Lys Thr Val Ala Pro Ala Glu Cys Ser
                210                 215
```

(2) INFORMATION FOR SEQ ID NO:6:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Trp Ser Cys Ile Ile Leu Phe Leu Val Ala Thr Ala Thr Gly
-19                 -15                 -10                  -5

Val His Ser Asp Ile Glu Leu Thr Gln Asp Pro Ala Val Ser Val Ala
         1               5                  10

Leu Gly Gln Thr Val Arg Ile Thr Cys Gln Gly Asp Ser Leu Arg Thr
     15                  20                  25

Tyr Tyr Ala Ser Trp Tyr Gln Gln Lys Pro Gly Gln Ala Pro Val Leu
 30                  35                  40                  45
```

```
Val Ile Tyr Gly Lys Asn Asn Arg Pro Ser Gly Ile Pro Asp Arg Phe
                50                  55                  60

Ser Gly Ser Ser Ser Gly Asn Thr Ala Ser Leu Thr Ile Thr Gly Ala
            65                  70                  75

Gln Ala Glu Asp Glu Ala Asp Tyr Phe Cys Asn Ser Gly Gly Lys Val
        80                  85                  90

Phe Gly Gly Gly Thr Lys Leu Thr Val Leu Gly Gln Pro Lys Ala Ala
    95                  100                 105

Pro Ser Val Thr Leu Phe Pro Pro Ser Leu Glu Glu Leu Gln Ala Asn
110                 115                 120                 125

Lys Ala Thr Leu Glu Glu Leu Gln Ala Asn Lys Ala Thr Leu Val Cys
                130                 135                 140

Leu Ile Ser Asp Phe Tyr Pro Gly Ala Val Thr Leu Ala Trp Lys Ala
                145                 150                 155

Asp Gly Arg Pro Val Lys Ala Gly Val Glu Thr Asn Lys Pro Ser Lys
                160                 165                 170

Gln Ser Asn Asn Lys Tyr Ala Ala Ser Ser Tyr Leu Ser Leu Thr Pro
                175                 180                 185

Glu Gln Trp Lys Ser His Arg Ser Tyr Ser Cys Gln Val Thr His Glu
190                 195                 200                 205

Gly Ser Thr Ala Glu Lys Thr Val Ala Pro Ala Glu Cys Ser
                210                 215
```

(2) INFORMATION FOR SEQ ID NO:7:

(i) SEQUENCE CHARACTERISTICS:
      (A) LENGTH: 1418 base pairs
      (B) TYPE: nucleic acid
      (C) STRANDEDNESS: single
      (D) TOPOLOGY: linear (ii) MOLECULE TYPE: other nucleic acid (ix) FEATURE:
      (A) NAME/KEY: CDS
      (B) LOCATION: 1..1418

(ix) FEATURE:
      (A) NAME/KEY: sig_peptide
      (B) LOCATION: 1..57

(ix) FEATURE:
      (A) NAME/KEY: mat_peptide
      (B) LOCATION: 58..1418
      (D) OTHER INFORMATION: /product= "IMMUNOGLOBIN, HEAVY
          CHAIN"

(xi) SEQUENCE DESCRIPTION: SEQ ID NO:7:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
-19         -15                 -10                 -5

GTC CAC TCC CAG GTC CAA CTG GAG CAG TGG GGC GCA GGA CTG TTG AAG      96
Val His Ser Gln Val Gln Leu Glu Gln Trp Gly Ala Gly Leu Leu Lys
            1               5                   10

CCT TCG GAG ACC CTG TCC CTC ACC TGC ACT GTC TAT GGT GGG TCC TTC     144
Pro Ser Glu Thr Leu Ser Leu Thr Cys Thr Val Tyr Gly Gly Ser Phe
        15                  20                  25

AGT GGT TAC TAC TGG AGC TGG ATC CGC CAG CCC CCA GGG AAG GGG CTG     192
Ser Gly Tyr Tyr Trp Ser Trp Ile Arg Gln Pro Pro Gly Lys Gly Leu
30                  35                  40                  45

GAG TGG ATT GGG GAA ATC AAT CAT AGT GGA AGC ACC AAC TAC AAC CCG     240
Glu Trp Ile Gly Glu Ile Asn His Ser Gly Ser Thr Asn Tyr Asn Pro
                50                  55                  60
```

```
TCC CTC AAG AGT CGA GTC ACC ATA TCA GTA GAC ACG TCC AAG AAC CAG        288
Ser Leu Lys Ser Arg Val Thr Ile Ser Val Asp Thr Ser Lys Asn Gln
             65                  70                  75

TTC TCC CTG AAA CTG AAC TCT GTG ACC GCC GCG GAC ACG GCT GTG TAT        336
Phe Ser Leu Lys Leu Asn Ser Val Thr Ala Ala Asp Thr Ala Val Tyr
         80                  85                  90

TAC TGT GCG AGG GCC CCA GAG TAT AAA TGG AAG TAT CAT GGG GAC TGG        384
Tyr Cys Ala Arg Ala Pro Glu Tyr Lys Trp Lys Tyr His Gly Asp Trp
     95                 100                 105

TTC GAC CCC TGG GGC CAA GGT ACC ACT GTC ACC GTC TCC TCA GCC TCC        432
Phe Asp Pro Trp Gly Gln Gly Thr Thr Val Thr Val Ser Ser Ala Ser
110                 115                 120                 125

ACC AAG GGC CCA TCG GTC TTC CCC CTG GCA CCC TCC TCC AAG AGC ACC        480
Thr Lys Gly Pro Ser Val Phe Pro Leu Ala Pro Ser Ser Lys Ser Thr
                130                 135                 140

TCT GGG GGC ACA GCG GCC CTG GGC TGC CTG GTC AAG GAC TAC TTC CCC        528
Ser Gly Gly Thr Ala Ala Leu Gly Cys Leu Val Lys Asp Tyr Phe Pro
            145                 150                 155

GAA CCG GTG ACG GTG TCG TGG AAC TCA GGC GCC CTG ACC AGC GGC GTG        576
Glu Pro Val Thr Val Ser Trp Asn Ser Gly Ala Leu Thr Ser Gly Val
        160                 165                 170

CAC ACC TTC CCG GCT GTC CTA CAG TCC TCA GGA CTC TAC TCC CTC AGC        624
His Thr Phe Pro Ala Val Leu Gln Ser Ser Gly Leu Tyr Ser Leu Ser
    175                 180                 185

AGC GTG GTG ACC GTG CCC TCC AGC AGC TTG GGC ACC CAG ACC TAC ATC        672
Ser Val Val Thr Val Pro Ser Ser Ser Leu Gly Thr Gln Thr Tyr Ile
190                 195                 200                 205

TGC AAC GTG AAT CAC AAG CCC AGC AAC ACC AAG GTG GAC AAG AAA GCA        720
Cys Asn Val Asn His Lys Pro Ser Asn Thr Lys Val Asp Lys Lys Ala
                210                 215                 220

GAG CCC AAA TCT TGT GAC AAA ACT CAG ACA TGC CCA CCG TGC CCA GCA        768
Glu Pro Lys Ser Cys Asp Lys Thr Gln Thr Cys Pro Pro Cys Pro Ala
            225                 230                 235

CCT GAA CTC CTG GGG GGA CCG TCA GTC TTC CTC TTC CCC CCA AAA CCC        816
Pro Glu Leu Leu Gly Gly Pro Ser Val Phe Leu Phe Pro Pro Lys Pro
        240                 245                 250

AAG GAC ACC CTC ATG ATC TCC CGG ACC CCT GAG GTC ACA TGC GTG GTG        864
Lys Asp Thr Leu Met Ile Ser Arg Thr Pro Glu Val Thr Cys Val Val
    255                 260                 265

GTG GAC GTG AGC CAC GAA GAC CCT GAG GTC AAG TTC AAC TGG TAC GTG        912
Val Asp Val Ser His Glu Asp Pro Glu Val Lys Phe Asn Trp Tyr Val
270                 275                 280                 285

GAC GGC GTG GAG GTG CAT AAT GCC AAG ACA AAG CCG CGG GAG GAG CAG        960
Asp Gly Val Glu Val His Asn Ala Lys Thr Lys Pro Arg Glu Glu Gln
                290                 295                 300

TAC AAC AGC ACT TAC CGG GTG GTC AGC GTC CTC AAA GTC CTG CAC CAG       1008
Tyr Asn Ser Thr Tyr Arg Val Val Ser Val Leu Lys Val Leu His Gln
            305                 310                 315

GAC TGG CTG AAT GGC AAG GAG TAC AAG TGC AAG GTC TCC AAC AAA GCC       1056
Asp Trp Leu Asn Gly Lys Glu Tyr Lys Cys Lys Val Ser Asn Lys Ala
        320                 325                 330

CTC CCA GCC CCC ATT GAG AAA ACC ATC TCC AAA GCC AAA GGG CAG CCC       1104
Leu Pro Ala Pro Ile Glu Lys Thr Ile Ser Lys Ala Lys Gly Gln Pro
    335                 340                 345

CGA GAA CCA CAG GTG TAC ACC CTG CCC CCA TCC CGG GAT GAG CTG ACC       1152
Arg Glu Pro Gln Val Tyr Thr Leu Pro Pro Ser Arg Asp Glu Leu Thr
350                 355                 360                 365

AAG AAC CAG GTC AGC CTG ACC TGC CTG GTC AAA GGT TTC TAT CCT AGC       1200
Lys Asn Gln Val Ser Leu Thr Cys Leu Val Lys Gly Phe Tyr Pro Ser
```

```
                    370                375                380
GAC ATC GCC GTG GAG TGG GAG AGC AAT GGG CAG CCG GAG ACC AAC TAC    1248
Asp Ile Ala Val Glu Trp Glu Ser Asn Gly Gln Pro Glu Thr Asn Tyr
            385                390                395

AAG ACC ACG CCT CCC GTG CTG GAC TCC GAC GGC TCC TTC TTC CTC TAC    1296
Lys Thr Thr Pro Pro Val Leu Asp Ser Asp Gly Ser Phe Phe Leu Tyr
            400                405                410

AGC AAG CTC ACC GTG GAC AAG AGC AGG TGG CAG CAG GGG AAC GTC TTC    1344
Ser Lys Leu Thr Val Asp Lys Ser Arg Trp Gln Gln Gly Asn Val Phe
            415                420                425

TCA TGC TCC GTG ATG CAT GAG GCT CTG CAC AAC CAC TAC ACG CAG AAG    1392
Ser Cys Ser Val Met His Glu Ala Leu His Asn His Tyr Thr Gln Lys
430                435                440                445

AGC CTC TCC CTG TCT CCG GGT AAA  TG                                1418
Ser Leu Ser Leu Ser Pro Gly Lys
            450

(2) INFORMATION FOR SEQ ID NO:8:

(i) SEQUENCE CHARACTERISTICS:
        (A) LENGTH: 472 amino acids
        (B) TYPE: amino acid
        (D) TOPOLOGY: linear (ii) MOLECULE TYPE: protein (xi) SEQUENCE DESCRIPTION: SEQ ID NO:8:

Met Gly Trp Ser Cys Ile Ile Leu Phe Leu Val Ala Thr Ala Thr Gly
-19             -15                 -10                 -5

Val His Ser Gln Val Gln Leu Glu Gln Trp Gly Ala Gly Leu Leu Lys
                1               5                  10

Pro Ser Glu Thr Leu Ser Leu Thr Cys Thr Val Tyr Gly Gly Ser Phe
        15                  20                  25

Ser Gly Tyr Tyr Trp Ser Trp Ile Arg Gln Pro Pro Gly Lys Gly Leu
30                  35                  40                  45

Glu Trp Ile Gly Glu Ile Asn His Ser Gly Ser Thr Asn Tyr Asn Pro
                50                  55                  60

Ser Leu Lys Ser Arg Val Thr Ile Ser Val Asp Thr Ser Lys Asn Gln
                65                  70                  75

Phe Ser Leu Lys Leu Asn Ser Val Thr Ala Ala Asp Thr Ala Val Tyr
            80                  85                  90

Tyr Cys Ala Arg Ala Pro Glu Tyr Lys Trp Lys Tyr His Gly Asp Trp
        95                  100                 105

Phe Asp Pro Trp Gly Gln Gly Thr Thr Val Thr Val Ser Ser Ala Ser
110                 115                 120                 125

Thr Lys Gly Pro Ser Val Phe Pro Leu Ala Pro Ser Ser Lys Ser Thr
                130                 135                 140

Ser Gly Gly Thr Ala Ala Leu Gly Cys Leu Val Lys Asp Tyr Phe Pro
            145                 150                 155

Glu Pro Val Thr Val Ser Trp Asn Ser Gly Ala Leu Thr Ser Gly Val
            160                 165                 170

His Thr Phe Pro Ala Val Leu Gln Ser Ser Gly Leu Tyr Ser Leu Ser
        175                 180                 185

Ser Val Val Thr Val Pro Ser Ser Ser Leu Gly Thr Gln Thr Tyr Ile
190                 195                 200                 205

Cys Asn Val Asn His Lys Pro Ser Asn Thr Lys Val Asp Lys Lys Ala
                210                 215                 220
```

```
Glu Pro Lys Ser Cys Asp Lys Thr Gln Thr Cys Pro Pro Cys Pro Ala
            225                 230                 235
Pro Glu Leu Leu Gly Gly Pro Ser Val Phe Leu Phe Pro Pro Lys Pro
            240                 245                 250
Lys Asp Thr Leu Met Ile Ser Arg Thr Pro Glu Val Thr Cys Val Val
            255                 260                 265
Val Asp Val Ser His Glu Asp Pro Glu Val Lys Phe Asn Trp Tyr Val
270                 275                 280                 285
Asp Gly Val Glu Val His Asn Ala Lys Thr Lys Pro Arg Glu Glu Gln
                290                 295                 300
Tyr Asn Ser Thr Tyr Arg Val Val Ser Val Leu Lys Val Leu His Gln
            305                 310                 315
Asp Trp Leu Asn Gly Lys Glu Tyr Lys Cys Lys Val Ser Asn Lys Ala
            320                 325                 330
Leu Pro Ala Pro Ile Glu Lys Thr Ile Ser Lys Ala Lys Gly Gln Pro
            335                 340                 345
Arg Glu Pro Gln Val Tyr Thr Leu Pro Pro Ser Arg Asp Glu Leu Thr
350                 355                 360                 365
Lys Asn Gln Val Ser Leu Thr Cys Leu Val Lys Gly Phe Tyr Pro Ser
                370                 375                 380
Asp Ile Ala Val Glu Trp Glu Ser Asn Gly Gln Pro Glu Thr Asn Tyr
            385                 390                 395
Lys Thr Thr Pro Pro Val Leu Asp Ser Asp Gly Ser Phe Phe Leu Tyr
            400                 405                 410
Ser Lys Leu Thr Val Asp Lys Ser Arg Trp Gln Gln Gly Asn Val Phe
            415                 420                 425
Ser Cys Ser Val Met His Glu Ala Leu His Asn His Tyr Thr Gln Lys
430                 435                 440                 445
Ser Leu Ser Leu Ser Pro Gly Lys
                450

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

CCTCAGTGAA GGTCTCCTGC AAGG                                            24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

TCCTGCGCTG GTGAAAGCCA CACA                                            24

(2) INFORMATION FOR SEQ ID NO:11:

(i) SEQUENCE CHARACTERISTICS:
```

(A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

GGTCCCTGAG ACTCTCCTGT GCA                                      23

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

TCGGAGACCC TGTCCCTCAC CTGCA                                    25

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

CGCTGTCTCT GGTTACTCCA TCAG                                     24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GAAAAAGCCC GGGGAGTCTC TGAA                                     24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

CCTGTGCCAT CTCCGGGGAC AGTG                                     24

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CAGTCTGTGC TGACTCAG                                                    18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

CACACYAGTG TRGCCTGGTT                                                  20

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

CCTGTCAGAT CTATGAACAT TCTGTAGGGG                                       30

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

CCGCCCTCCC TCGAGCTTCA A                                                21

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CASTCTGAGC TCACKCAG                                                    18

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

-continued

```
TTGAAGCTCG AGGGAGGGCG GGAA                                          24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

CAAGGTACCA CGGTCACCGT CTCC                                          24

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

GAAGATCTCA TTTACCCGGA GACAGGGAG                                     29

(2) INFORMATION FOR SEQ ID NO:24:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

GTCCAACTGC AGCAGTGGGG CGCAGGACTG TTGAAGCCTT CGGAGACCCT GTCCCTC      57

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

TGAGGAGACG GTGACCGTGG TACCTTGGC                                     29
```

16. The recombinant monoclonal antibody according to claim 14, wherein the polypeptide sequence of its light chain and the polypeptide sequence of its heavy chain are human sequences.

17. The recombinant monoclonal antibody according to claim 14, wherein said recombinant monoclonal antibody belongs to the IgG class.

18. A pharmaceutical composition comprising the recombinant monoclonal antibody according to claim 14, for the production of medicaments.

19. A method for preventing the hemolytic disease of newborn, wherein said method comprises injecting into a Rhesus negative woman immediately after childbirth or abortion, the recombinant monoclonal antibody according to claim 14, in an amount effective to induce the lysis of Rh-positive foetal red blood cells which are present in the maternal blood.

20. The DNA fragment of claim 1, wherein the DNA fragment in (a) is SEQ ID NO:1.

21. The DNA fragment of claim 1, wherein the DNA fragment in (b) is SEQ ID NO:3.

22. The DNA fragment of claim 1, wherein the amino acid sequence in (c) contains a substitution of Glu-Ser-Val for Asp-Ile-Glu at positions 1–3 of SEQ ID NO:2.

23. The DNA fragment of claim 1, wherein the amino acid sequence in (d) contains a substiution of Ala for Thr at position 23 of SEQ ID NO:4.

24. The expression cassette according to claim 2, wherein the sequence encoding the constant domain of the light chain or the heavy chain of an immunoglobulin is a human sequence.

25. The expression cassette according to claim 2, wherein the baculovirus promoter is a polyhedrin promoter or a p10 promoter.

26. The recombinant vector according to claim 5, wherein said expression cassette is flanked by sequences of the regions flanking the p10 gene in the wild-type baculovirus or the polyhedrin gene in the wild-type baculovirus.

27. The recombinant vector of claim 5, wherein said recombinant vector comprises the expression cassette containing the gene encoding the light chain of the r-D7C2 antibody which is flanked by sequences of the regions flanking the polyhedrin gene in the wild-type baculovirus; and the expression cassette containing the heavy chain of the r-D7C2 antibody which is flanked by sequences of the regions flanking the p10 gene in the wild-type baculovirus.

28. The recombinant baculovirus of claim 6, wherein the transcription of the sequence encoding the light chain of the r-D7C2 antibody is under the control of the polyhedrin promoter, and the transcription of the sequence encoding the heavy chain of the r-D7C2 antibody is under the control of the p10 promoter.

* * * * *